(12) United States Patent
Mihailescu et al.

(10) Patent No.: US 7,732,773 B2
(45) Date of Patent: Jun. 8, 2010

(54) GAMMA-RAY TRACKING METHOD FOR PET SYSTEMS

(75) Inventors: Lucian Mihailescu, Pleasanton, CA (US); Kai M. Vetter, Alameda, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 20 days.

(21) Appl. No.: 11/649,081

(22) Filed: Dec. 29, 2006

(65) Prior Publication Data

US 2007/0253530 A1 Nov. 1, 2007

Related U.S. Application Data

(60) Provisional application No. 60/755,470, filed on Dec. 29, 2005, provisional application No. 60/755,469, filed on Dec. 29, 2005.

(51) Int. Cl.
*G01T 1/172* (2006.01)

(52) U.S. Cl. .................................. 250/363.04

(58) Field of Classification Search ............ 250/363.02, 250/363.04
See application file for complete search history.

(56) References Cited

U.S. PATENT DOCUMENTS

| | | | |
|---|---|---|---|
| 6,782,342 B2 * | 8/2004 | LeGore et al. | 702/181 |
| 2002/0008205 A1 * | 1/2002 | Kurfess et al. | 250/370.13 |
| 2005/0286749 A1 * | 12/2005 | De Man et al. | 382/131 |

* cited by examiner

*Primary Examiner*—David P Porta
*Assistant Examiner*—Marcus H Taningco
(74) *Attorney, Agent, or Firm*—John P. Wooldridge; John H. Lee

(57) ABSTRACT

Gamma-ray tracking methods for use with granular, position sensitive detectors identify the sequence of the interactions taking place in the detector and, hence, the position of the first interaction. The improved position resolution in finding the first interaction in the detection system determines a better definition of the direction of the gamma-ray photon, and hence, a superior source image resolution. A PET system using such a method will have increased efficiency and position resolution.

6 Claims, 5 Drawing Sheets

GAMMA-RAY TRACKING METHOD FOR PET SYSTEMS

This application claims priority to U.S. Provisional Patent Application Ser. No. 60/755,470, titled "Gamma-Ray Tracking Method for Pet Systems" filed Dec. 29, 2005, and to U.S. Provisional Patent Application Ser. No. 60/755,469, titled: "Methods for Increasing Sensitivity of Gamma-Ray Imagers" filed Dec. 29, 2005, both incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to gamma ray detection, and more specifically, it relates to techniques for tracking gamma rays.

2. Description of Related Art

Positron Emission Tomography (PET) is a very important tool used for medical diagnostics and research. A PET system of increased spatial resolution and efficiency will be of great impact, particularly on small animal imaging, where the features that need to be identified are in the range of millimeters.

The spatial resolution in most of the state-of-the-art PET systems is limited by two factors: 1) the dimension of the scintillating pixels used in the detector arrays, and 2) the Compton scatterings that the gamma-ray undergoes in the detector array before being absorbed in a photoelectric interaction. The use of heavy scintillators helps reduce the fraction of Compton scatterings, and the average length between scatterings, but Compton scatterings are still important.

Position sensitive semiconductor detectors, especially the double sided segmented planar detectors, are alternatives to scintillator arrays. Such detectors have the advantage of a 3D position sensitivity, and potentially superior position resolution and granularity. The introduction of the planar Ge detectors with orthogonal strip segments has allowed the development of new, compact and efficient Compton scatter imagers. These detectors are characterized by a superior energy resolution. Position sensitivity is provided by the orthogonal strip segments of around 2 mm pitch. Despite a limited segment pitch size of 2 mm, position resolution in the sub-millimeter range is demonstrated by using new waveform filtering methods. Some of the methods employed to make that possible are described in U.S. patent application Ser. No. 11/607,554, titled: "Methods for Increasing the Sensitivity of Gamma-Ray Imagers,") filed Nov. 30, 2006, using Express Mail label number EV424773615US, incorporated herein by reference. Position sensitive detectors normally used in PET systems provide good intrinsic position resolution, but do not correct for multiple interactions caused by Compton scatterings of the 511 keV annihilation photon in the detector.

SUMMARY OF THE INVENTION

It is an object of the present invention to provide a method for determining which photon interaction of said a plurality of photon interactions in a detector or detector segment of a PET system has the highest probability of being the first photon interaction in the detector or detector segment.

It is another object to reduce the blurring effects in the image produce by a PET system by reducing or eliminating photons scattered within the sample.

These and other objects will be apparent based on the disclosure herein.

A method to increase imaging sensitivity for PET scanners improves the imaging resolution by removing the blurring effects created by the photons interacting multiple times. In order for the methods to be effective, the PET scanners must have good position resolution and granularity, i.e., capability to identify several interactions taking place in the gamma-ray detector. Bayesian statistics is used to identify the point of the first interaction by determining the photon scattering sequence with the highest likelihood of occurrence. If at least one photon multiply scatters in the detector, it is possible to identify photons that have scattered in the sample, before interacting in the detection system. In this way, the image contrast is also improved. The presented methods work with fully absorbed photons as well as with scatter photons (from the Compton background).

The methods presented here make use of the data available in a high granularity, high position resolution detection system to determine more accurately the direction of the incident annihilation gamma-rays by finding the most likely scattering sequence of the gamma-ray photon in the detection system, when the gamma-ray interacts multiple times in the detector. This will make available for high resolution imaging photons that otherwise would have been rejected, or would have provided poor image quality. The position sensitive detectors can be either scintillators or semiconductor detectors. However, the detectors must be able to provide acceptable granularity of detection, i.e., they must be able to provide the positions and energies of multiple interactions taking place in the detection system. A finer detection granularity will increase the efficiency of the proposed event reconstruction methods. Previous methods for gamma-ray interaction sequencing were developed for nuclear physics experiments, and for Compton cameras. The methods presented here are optimized for PET scanners.

The invention includes a method that can be programmed onto a computer readable medium. An embodiment of the method comprises the steps of listing each position within a first volume of at least two photon interactions of a first plurality of photon interactions resulting from a first annihilation gamma-ray and determining which photon interaction of the at least two photon interactions has the highest probability of being the first photon interaction in the first volume. The first volume can comprise at least one detector and specifically may be a DSSD. Generally simultaneously with the above steps, the method further comprises listing the position within a second volume facing the sample of a second at least two photon interactions of a second plurality of photon interactions produced by a second annihilation gamma-ray emitted at about 180 degrees from the first annihilation gamma-ray, where the sample is located between the first volume and the second volume; and determining which photon interaction of the second at least two photon interactions has the highest probability of being the first photon interaction in the second volume. The highest probability of being the first photon interaction in the first volume is determined with Bayesian probability theory and where the highest probability of being the first photon interaction in the second volume is determined with Bayesian probability theory. When the first photon interaction in the first volume has an energy of less that 511 keV, the first photon interaction in the first volume is assigned a low reliability index and where when the first photon interaction in the second volume has an energy of less that 511 keV, the first photon interaction in the second volume is assigned a low reliability index. The step of listing each position of at least two photon interactions of a first plurality of photon interactions within a first volume comprises collecting a first set of gamma-ray photon interaction produced data from at least one electrode segment of a first double-sided segmented detector (DSSD) and calculating, using the first set of gamma-ray photon interaction produced data, a 3 dimensional position of the gamma-ray photon interaction in the first DSSD, and where the step of listing each position of at least two photon interactions of a second plurality of photon interactions within a second volume comprises collecting a second set of gamma-ray photon interaction produced data from at least one electrode segment of a second double-sided segmented detector (DSSD) and calculating, using the second set of gamma-ray photon interaction produced data, a 3 dimensional position of the gamma-ray photon interaction in the second DSSD.

An improved PET system using the proposed methods will be of useful for biomedical investigations of interest for DOE and DHS. Spin-off algorithms can be used in gamma-ray imaging devices, such as Compton cameras, coded apertures and SPECT systems. An improved small animal PET system of increased resolution and sensitivity will be of great interest in biomedical research. Research laboratories, universities and drug manufacturing companies are potential users. A large PET system using the proposed methods will be of interest for biomedical research, as well as for clinical investigations.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

A PET detection system is a coincidence system that aims to detect two annihilation gamma-rays emitted at about 180 degrees from each other by a β+ radioactive tracer located inside a sample. The positions of the first interactions are used to reconstruct the direction of the two annihilation gamma-rays. This direction forms a line of projection, sometimes referred to as a line-of-response (LOR). By acquiring multiple such events, the distribution of the tracer inside the sample is reconstructed by analyzing the intersection of the corresponding projection lines.

The methods presented here make use of the data available in a high granularity, high position resolution detection system to determine more accurately the position where the photon interacted first in the detection system. This is achieved by finding the most likely scattering sequence of the gamma-ray photon in the detection system, when the gamma-ray interacts multiple times in the detector. This is made possible by using a gamma-ray tracking algorithm as described below. The algorithm takes as input the list of interaction vertices provided by a position sensitive detector. Six values are associated to each vertex: a 3-dimensional position vector (r), the deposited energy (E), the index of the detector hit (D), and, if available, a factor characterizing the reliability of the identified interaction (ρ). The factor ρ indicates whether the identified vertex is a single, clean interaction or two overlapping interactions. Overlapping interactions are herein referred to as the interactions that take place within the same detection element, such as a segment For each event, the gamma-ray tracking algorithm will provide the vertex of the first Compton scattering and the likelihood associated with the identified vertex.

Figure 1:
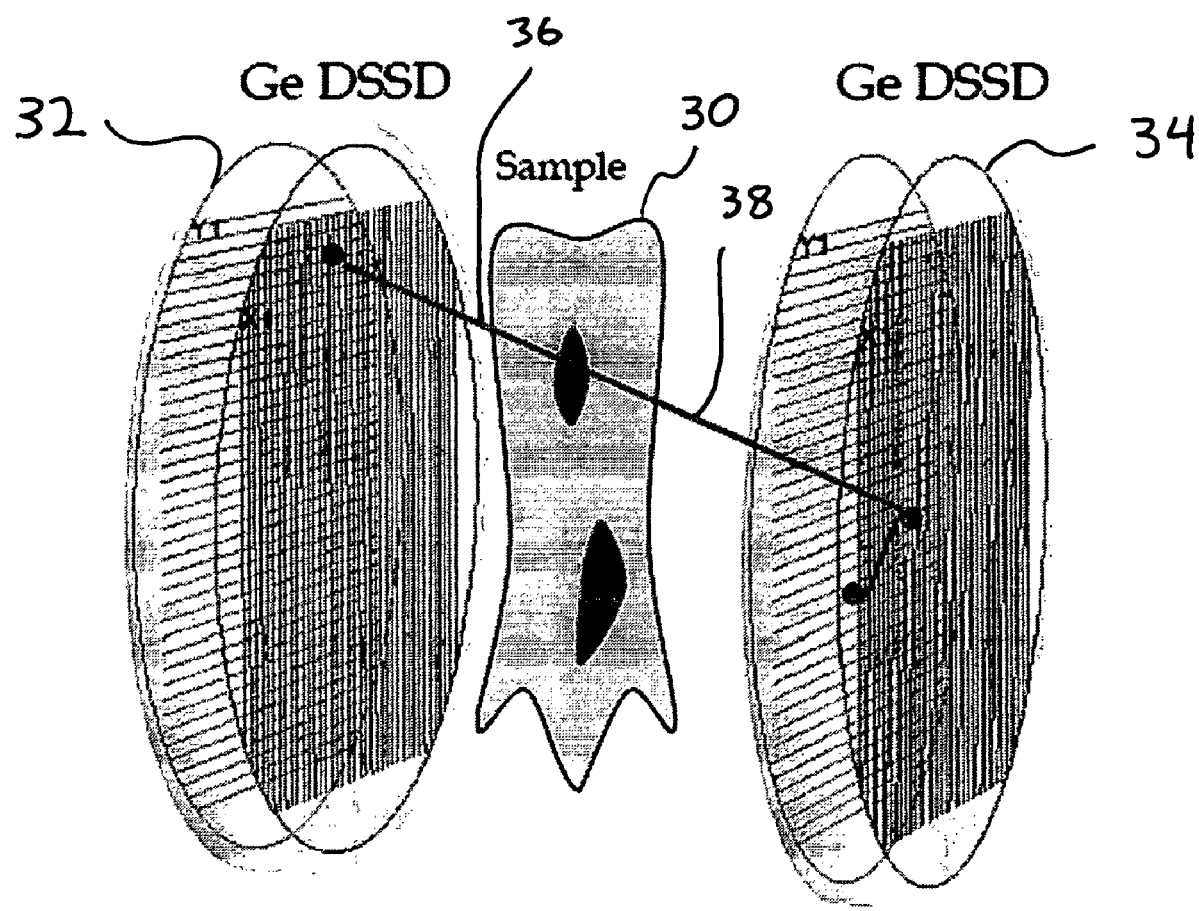
FIG. 1 shows a system of two double sided segmented planar Ge detectors acting as a PET system.
Figure 2:
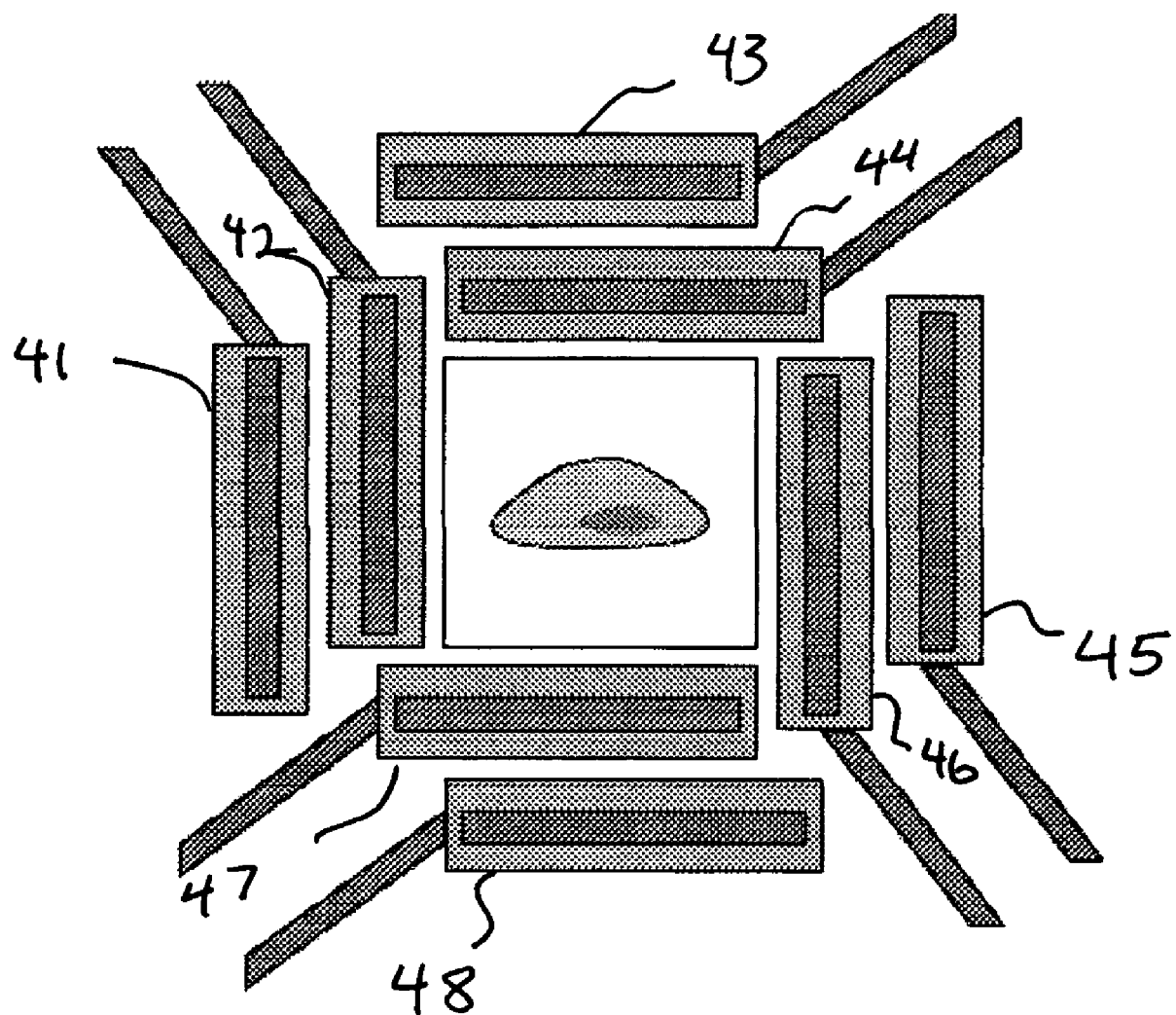
FIG. 2 shows a system of eight double sided segmented planar Ge detectors in a small animal PET system.

FIGS. 1 and 2 show examples of PET implementations that are suitable to use with the methods described here. These are systems of 2 and 8 Ge planar double sided segmented detectors (DSSDs), respectively. FIG. 1 shows a sample 30 located between two Ge double sided segmented detectors 32, 34. The radioactive tracer generates the two coincident annihilation gamma-rays 36, 38. FIG. 2 shows a system that includes eight (8) detectors 41-48. DSSDs have the capability to provide good position resolution and granularity without compromising the energy resolution; however, any type of detector can work, as long as it provides good granularity, position and energy resolution.

Bayesian statistics are used to estimate the most likely scattering sequence for both coincident photons. According to the Bayes theorem, the conditional probability for a certain model, $M_i$, given a set of data, X, is expressed as:

$$P(M_i \mid X) = \frac{P(M_i)P(X \mid M_i)}{P(X)} = \frac{P_i}{\sum_j P_j}. \quad (1)$$

$P(M_i)$ is the prior probability known about the model $M_i$. $P(X|M_i)$ is the conditional probability for data X given model $M_i$, and $P(X)$ is the probability of occurrence of data X. If all possible models are known for a given set of data, $P(X)$ can be calculated as the sum over all models:

$$P(X) = \sum_j P(M_j)P(X \mid M_j). \quad (2)$$

This probability will provide the normalization factor for $P(M_i/X)$, which is important in assessing the reliability of the reconstructed event.

In the present case, the model $M_i$, is defined by a scattering sequence associated with each of the two coincident photons and a total energy for each incident photon of 511 keV. This is the energy of the (e+e−) annihilation gamma-ray. If no Compton scatterings take place in the sample, the measured event will be consistent with the model for which the incident gamma-ray is 511 keV. The calculation of a probability for this model will finally either confirm or reject the model. At the end, the model with the highest probability will determine the scattering sequence for the two photons, and whether the two incident photons have Compton scattered in the sample or not.

When the 511 keV photon Compton scatters in the sample, the photon impinging on the detector can have an energy $E_{total}$ smaller than 511 keV. Using the tracking algorithm, it will be possible to estimate $E_{total}$ by resolving the kinematics in the Compton scatterings at the first assumed interaction:

$$E_{total,k} = \frac{E_{int,k}}{2}\left(1 + \sqrt{1 + \frac{4m_0 c^2}{E_{int,k}(1-\cos\theta_k)}}\right)\ldots \quad (3)$$

Figure 3:
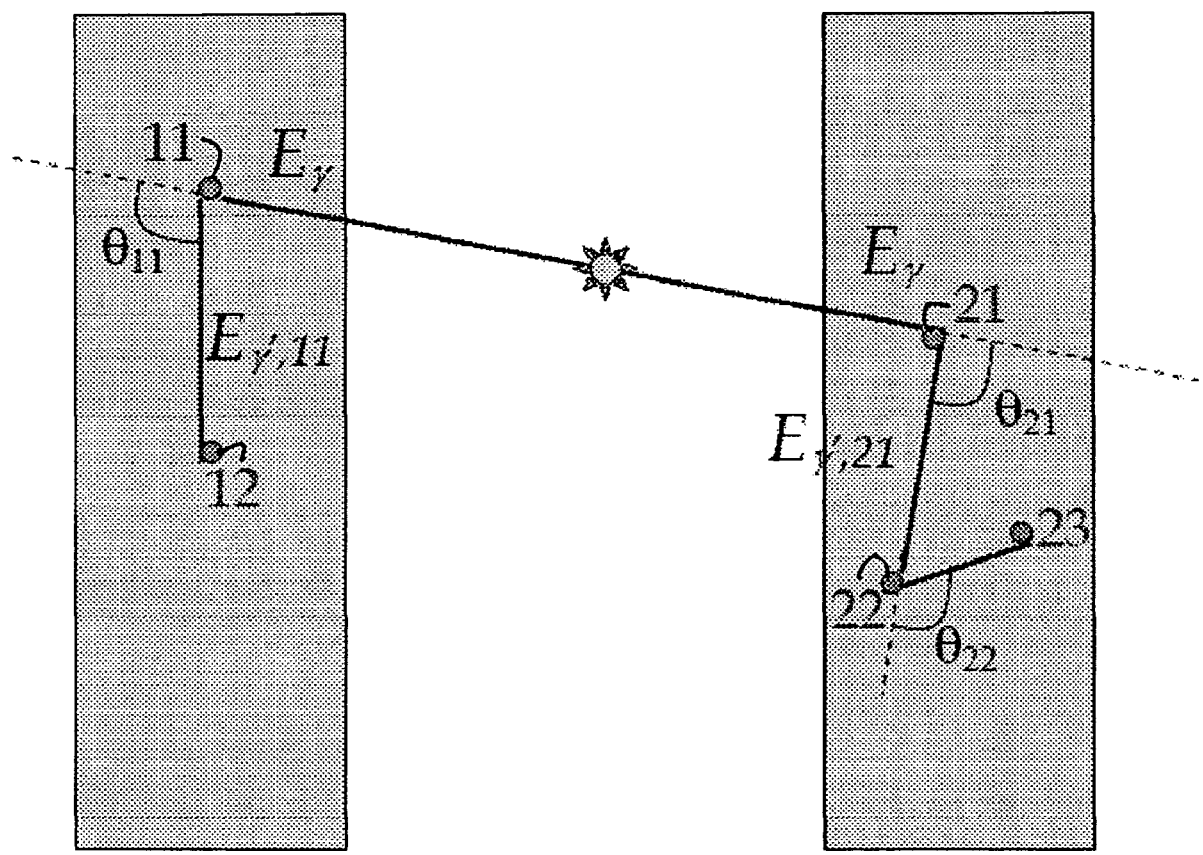
FIG. 3 shows an example coincident event.

Here, $\theta_k$ is the measured gammed-ray scattering angle for the assumed sequence for photon k (k=1,2), $m_0$, is the rest mass of the electron. The scattering angles are determined by the direction made by the first assumed interaction points for the two photons, and the direction of the scattering photon k (direction made by interaction points 11 and 12 for photon k=1, and interaction points 21 and 22 for photon k=2 in FIG. 3). The calculation of the probability of a model given the observed interactions uses the probability density function for the calculated energies $E_{total,k}$ as determined by the propagation of the uncertainties of the parameters in the right side of Equation 3. Assuming a normal distribution for the spread of the total energy as calculated using the Compton scattering formula, $E_{total,k}^{(c)}$, around the modeled $E_{total,k}$, the $P(X|M_i)$ term becomes:

$$P(X|M_i) = \frac{1}{\sigma_{E_1}\sigma_{E_2} 2\pi} e^{-\left(\frac{(m_e c^2 - E_{total,1})^2}{\sigma_{E_1}^2} + \frac{(m_e c^2 - E_{total,2})^2}{\sigma_{E_2}^2}\right)} \quad (4)$$

If the spread of the total energy is assumed to be a Lorentz distribution of width $\sigma_{Ek}$, the term $P(X|M_{i,k})$ is calculated by integrating the probability density function $f(E)$:

$$P(X|M_{i,k}) = \int_{E_{total,k}-\sigma_k/2}^{E_{total,k}+\sigma_k/2} f(E)dE = \quad (5)$$

$$\int_{E_{total,k}-\sigma_k/2}^{E_{total,k}+\sigma_k/2} \frac{\sigma_k}{2\pi\left[(m_e c^2 - E)^2 + \left(\frac{\sigma_k}{2}\right)^2\right]} dE.$$

Then, $P(X|M_i)$ is the product of the two probabilities $P(X|M_{i,k})$, with k=1,2:

$$P(X|M_i) = \frac{1}{\pi^2}\text{atan}\left(\frac{1}{2\frac{(m_e c^2 - E_{total,1})^2}{\sigma_{E_1}^2}}\right)\text{atan}\left(\frac{1}{2\frac{(m_e c^2 - E_{total,2})^2}{\sigma_{E_2}^2}}\right). \quad (6)$$

The advantage of a Lorentz distribution is that its longer tails better approximate the spread determined by the Compton profile of bounded electrons.

Other competing models account for sequences that contain vertices of multiple overlapping interactions. In the present approach, the events that are likely to be described by such models are rejected.

Once the model is defined, $P(M_i)$ can be calculated by accounting for the individual probabilities of the gamma-ray to go $L_{j-1,j}$ distance through the detector between two successive interactions without being absorbed, and then, interacting within an arbitrary interval $\delta$ either in a Compton scattering, or in a photoelectric effect if the model assumes that the current interaction is the last in the event, i.e., a photoelectric absorption.

$$P(M_i) = \prod_{k=1}^{2}\prod_{j=1}^{N} P_{L,j,k} P_{C,Ph,j,k}. \quad (7)$$

The individual probabilities $P_{L,j,k}$ become:

$$P_{L,j,k} = \int_{L_{(j-1,j),k}}^{L_{(j-1,j),k}+\delta} \mu_{total,j,k} e^{-\mu_{total,j,k} x} dx \quad (8)$$

$$= \left(1 - e^{\mu_{total,j,k}\delta}\right)e^{-\mu_{total,j,k} L_{(j-1,j),k}}$$

$$\cong \mu_{total,j,k}\delta \cdot e^{-\mu_{total,j,k} L_{(j-1,j),k}}$$

$$= P_{interaction,k} \cdot P_{propagation,k}$$

Whereas the probability for Compton scattering is determined by the factor:

$$P_{C,j,k} = \frac{\mu_{KN,j,k}}{\mu_{total,j,k}} \frac{\mu_{KN(\theta),j,k}}{\mu_{KN,j,k}}, \quad (9)$$

The probability for a photoelectric interaction is:

$$P_{Ph,j,k} = \frac{\mu_{Ph,j,k}}{\mu_{total,j,k}} \ldots \quad (10)$$

Figure 4:
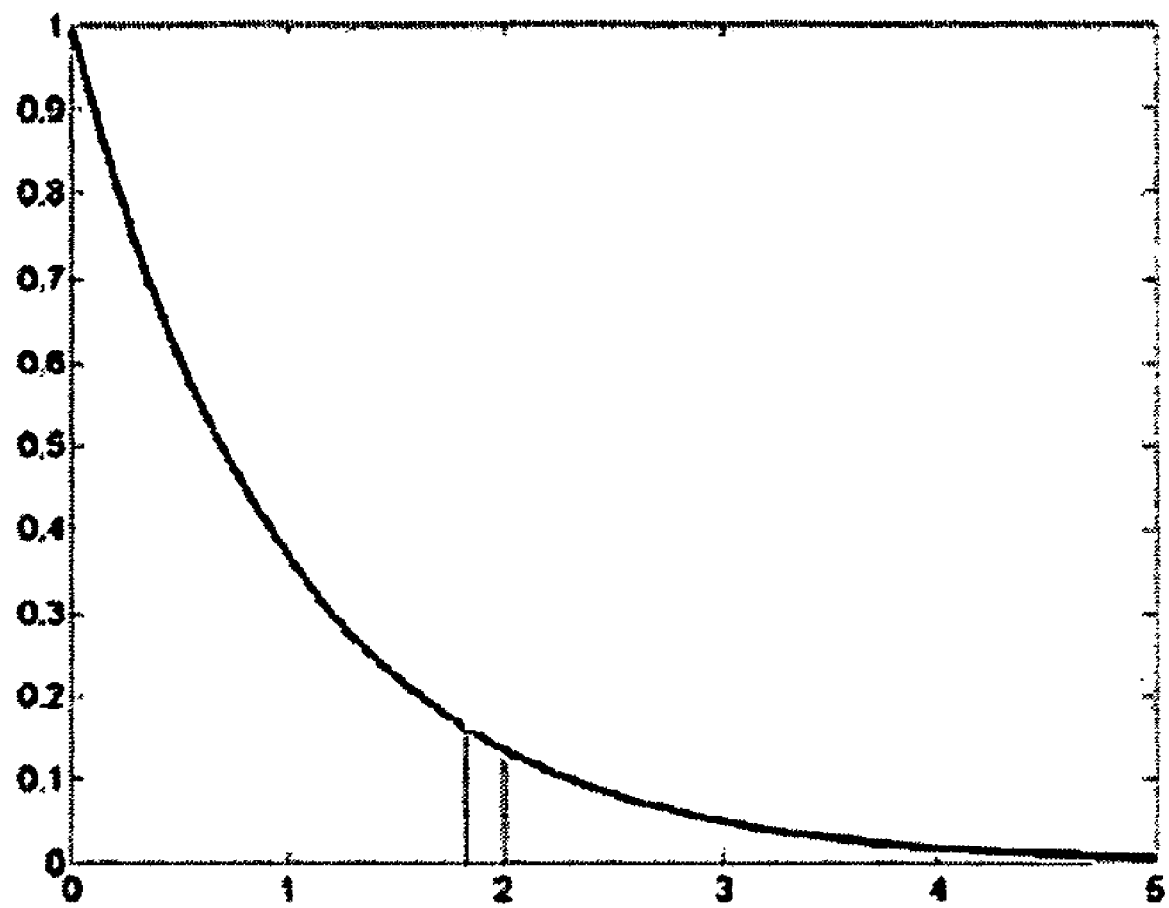
FIG. 4 shows an attenuation curve for a photon in the detector.

$\mu_{total,j,k}$ is the total attenuation coefficient ($\mu_{total,j,k} = \mu_{Ph,j,k} + \mu_{KN,j,k}$), $\mu_{Ph,j,k}$ is the photoelectric absorption coefficient, $\mu_{KN,j,k}$ is the total Compton absorption coefficient, and $\mu_{KN(\theta),j,k}$ is the equivalent absorption coefficient for a Compton scattering at angle $\theta$. FIG. 4 shows an attenuation curve for a photon in the detector. $\mu_{KN(\theta),j,k}$ is calculated using the Klein-Nishina differential cross section for the Compton scattering:

$$\mu_{KN(\theta),j,k} \propto \frac{\partial \sigma}{\partial \cos\theta}\delta\cos\theta = \quad (11)$$

$$\pi r_0 \frac{E_{scat,j,k}}{E_{0,j,k}}\left[\frac{E_{0,j,k}}{E_{scat,j,k}} + \frac{E_{scat,j,k}}{E_{0,j,k}} - \sin^2\theta\right]\delta\cos\theta.$$

The total Compton scattering coefficient is:

$$\mu_{KN,j,k} \propto \int_{-1}^{1} \frac{\partial \sigma}{\partial \cos\theta} d\cos\theta. \quad (12)$$

Finally, introducing $P(M_i)$ and $P(X|M_i)$ in $P_i$, the likelihood of the model becomes:

$$P_i = P_{interactions\_i} \cdot P_{propagation\_i} \cdot P_{kinematics\_i} \quad (13)$$

$$P_{interactions\_i} = \prod_{k=1}^{2}\prod_{inter\_j}\left(1 - e^{-\mu_{total,j,k}\delta}\right)\frac{\mu_{KN,j,k}}{\mu_{total,j,k}}\frac{\mu_{KN(\theta),j,k}}{\mu_{KN,j,k}},$$

-continued $$P_{propagation\_i} = e^{-\sum_{k=1}^{2}\sum_{inter\_i} k_{total,j,k} L_{(j-1,j),k}},$$

$$P_{kinematics\_i} = \frac{1}{\prod_{k=1}^{2}\sigma_{E_{j,k}}\sqrt{2\pi}} e^{-\sum_{k=1}^{2}\sum_{interm\_inter\_i}\frac{\left(E_{total,j,k}-E_{total,j,k}(c)\right)^2}{\sigma_{E_{j,k}}^2}}.$$

Monte Carlo simulated events were used for testing the described algorithms. A large, double sided segmented Ge detector was assumed as detection system.

The results show that the proposed tracking algorithm succeeds to reliably make available for imaging the events that consist of multiple interactions. The simulation results indicate that 60% more events can be made available for imaging.

Figure 5:
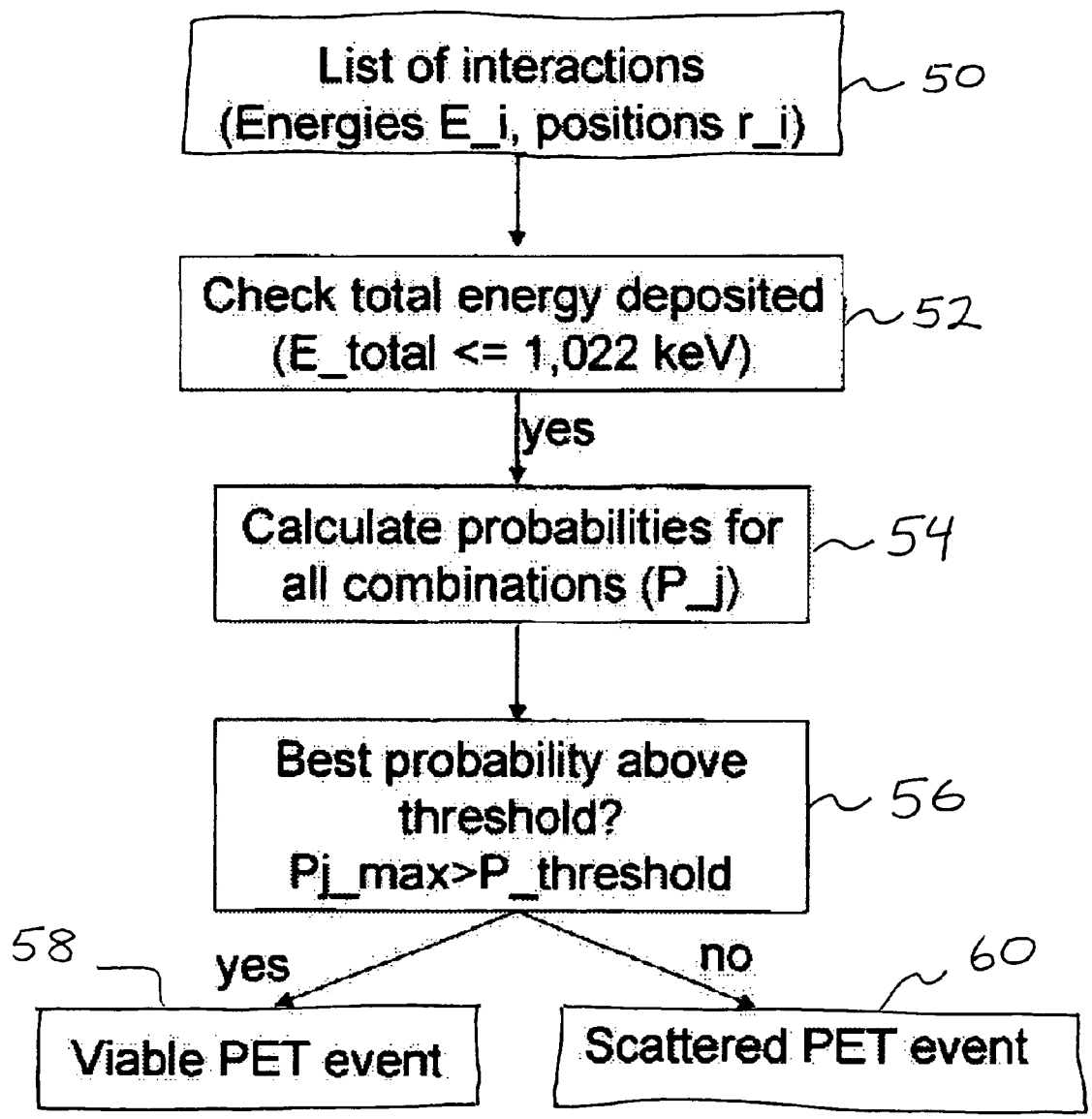
FIG. 5 shows an exemplary flow chart of analysis steps used for PET imaging using Bayesian statistics.

Thus, the algorithm, as generally depicted in FIG. 5, generates a list of the interactions (50) including their energies and positions, checks to see if the total energy deposited is less than or equal to 1,022 keV (52) and if it is equal to 1,022 keV, then the probabilities are calculated for all possible combinations (54). The best probability is then calculated (56) and a determination is made whether the interaction is to be considered a viable event (58) or a scattered event (60). The viable events are then usable for imaging.

A digital computer system can be programmed to perform the method of this invention. Once programmed to perform particular functions pursuant to instructions from program software that implements the method of this invention, such digital computer system in effect becomes a special-purpose computer particular to the method of this invention. The techniques necessary for this are well-known to those skilled in the art of computer systems.

Computer programs implementing the method of this invention will commonly be distributed to users on a distribution medium such as floppy disk or CD-ROM. From there, they will often be copied to a hard disk or a similar intermediate storage medium. When the programs are to be run, they will be loaded either from their distribution medium or their intermediate storage medium into the execution memory of the computer, configuring the computer to act in accordance with the method of this invention. All these operations are well-known to those skilled in the art of computer systems.

The term "computer-readable medium" encompasses distribution media, intermediate storage media, execution memory of a computer, and any other medium or device capable of storing for later reading by a computer a computer program implementing the method of this invention.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A method, comprising:
    positioning a radioactive tracer inside a sample, wherein said tracer interacts with said sample to emit a first annihilation gamma-ray and a second annihilation gamma-ray, wherein said first annihilation gamma-ray and said second annihilation gamma-ray are emitted at about 180 degrees from each other;
    intercepting said first annihilation gamma-ray with a first position sensitive detector (PSD), wherein said first annihilation gamma-ray produces a first plurality of photon reactions comprising a first photon reaction A in said first PSD and at least one subsequent photon reaction A' in said first PSD;
    intercepting said second annihilation gamma-ray with a second PSD, wherein said second annihilation gamma-ray produces a second plurality of photon reactions comprising a first photon reaction B in said second PSD and at least one subsequent photon reaction B' in said second PSD;
    determining, with a Bayesian probability theory based gamma-ray tracking algorithm, which photon of said first plurality of photon reactions has the highest probability of being said first photon reaction A;
    determining, with said gamma-ray tracking algorithm, which photon of said second plurality of photon reactions has the highest probability of being a first photon reaction B; and
    producing a line of response between said first photon reaction A and said first photon reaction B.

2. The method of claim 1, wherein said first PSD is an element of a positron emission tomography system.

3. The method of claim 1, wherein said first PSD comprises at least one double sided segmented detector.

4. The method of claim 1, wherein said second PSD comprises at least one double sided segmented detector.

5. The method of claim 1, further comprising determining a plurality of lines-of-response between a plurality of photon interactions in said first PSD and said second PSD and forming an image from said plurality of lines-of-response.

6. The method of claim 1, wherein when said first photon reaction A has an energy of less than 511 keV, said first photon reaction A is assigned a first low reliability index and wherein when said first photon reaction B in said second PSD has an energy of less than 511 keV, said first photon reaction B is assigned a second low reliability index.

* * * * *